(12) United States Patent
Tel-Ari

(10) Patent No.: US 9,161,961 B2
(45) Date of Patent: Oct. 20, 2015

(54) THERAPEUTIC COMPOSITIONS

(71) Applicant: Ruben Tel-Ari, Tel Aviv (IL)

(72) Inventor: Ruben Tel-Ari, Tel Aviv (IL)

( * ) Notice: Subject to any disclaimer, the term of this patent is extended or adjusted under 35 U.S.C. 154(b) by 0 days.

(21) Appl. No.: 13/751,499

(22) Filed: Jan. 28, 2013

(65) Prior Publication Data

US 2013/0195998 A1 Aug. 1, 2013

(30) Foreign Application Priority Data

Jan. 29, 2012 (IL) .......................................... 217807

(51) Int. Cl.
| | | |
|---|---|---|
| *A61K 36/61* | (2006.01) | |
| *A61K 33/30* | (2006.01) | |
| *A61K 33/34* | (2006.01) | |
| *A61K 31/315* | (2006.01) | |
| *A61K 31/555* | (2006.01) | |

(52) U.S. Cl.
CPC ............... *A61K 36/61* (2013.01); *A61K 31/315* (2013.01); *A61K 31/555* (2013.01); *A61K 33/30* (2013.01); *A61K 33/34* (2013.01)

(58) Field of Classification Search
None
See application file for complete search history.

(56) References Cited

U.S. PATENT DOCUMENTS

| | | | |
|---|---|---|---|
| 5,017,367 A | 5/1991 | Stojkoski | |
| 5,738,863 A | 4/1998 | Sackin et al. | |
| 5,965,145 A | 10/1999 | Marion et al. | |
| 6,551,606 B1 | 4/2003 | Golz-Berner et al. | |
| 7,147,876 B2 | 12/2006 | Riley et al. | |
| 7,563,461 B2 * | 7/2009 | Modak et al. | 424/641 |
| 2006/0105000 A1 * | 5/2006 | Friedman | 424/400 |
| 2010/0056430 A1 | 3/2010 | Lester | |
| 2010/0173007 A1 | 7/2010 | Dileva | |
| 2010/0178284 A1 | 7/2010 | Borden et al. | |
| 2010/0247376 A1 | 9/2010 | Yuros | |
| 2010/0273870 A1 | 10/2010 | Gao et al. | |
| 2011/0135746 A1 | 6/2011 | Triplett et al. | |
| 2011/0293757 A1 | 12/2011 | Riley et al. | |
| 2012/0009284 A1 | 1/2012 | Barnhill, Jr. | |

FOREIGN PATENT DOCUMENTS

WO 2009125383 A1 10/2009

OTHER PUBLICATIONS

Prairie, "Aqueous Topical Formulations" Dec. 18, 2004.*
Google search page with date of Prairie, printed 2014.*
Dextrose, revised Aug. 2010; http://www.dailymed.nlm.nih.gov/dailymed/archives/fdaDrugInfo.cfm?archiveid=27193.*
Henley et al., Prepubertal Gynecomastia Linked to Lavender and Tea Tree Oils, New England Journal of Medicine, 2007, pp. 479-485, vol. 356, No. 5.

\* cited by examiner

*Primary Examiner* — Ileana Popa
*Assistant Examiner* — Alissa Prosser

(57) ABSTRACT

The present invention discloses a non-irritating tea tree oil (TTO)-based topical therapeutic composition useful for both veterinary and human dermatology. The composition comprises a homogeneous mixture of TTO, 0.05 to 1.0% (wt/wt); at least one hypertonic composition providing the said TTO-based composition to 1700 to 2500 mOsm/L, 10 to 60% (wt/wt); and inorganic salts, 0.01% to 0.50% (wt/wt) and it is characterized by an effective, rapid & wide spectrum of action while being non-irritant to patient skin.

3 Claims, 8 Drawing Sheets

THERAPEUTIC COMPOSITIONS

FIELD OF THE INVENTION

The present invention pertains to a therapeutic composition useful for cosmetics and for both veterinary and human and medicine.

BACKGROUND OF THE INVENTION

Tea tree oil, or melaleuca oil, is a pale yellow color to nearly colorless and clear essential oil with a fresh camphoraceous odor. Tea tree oil composition, as per ISO 4730 (2004) is as follows: terpinen-4-ol 30-48%; γ-terpinene 10-28%; α-terpinene 5-13%; 1,8-Cineole 0-15%; α-terpinolene 1.5-5%; α-terpineol 1.5-8%; α-pinene 1-6%; and p-cymene 0.5-8%. For sake of clarity, the terms Tea tree oil and TTO will interchangeably refer hereinafter the various possible TTO compositions as a whole, and to each of its ingredients separately.

Many patents disclose the use of TTO in medicine, some of the recent ones are US 20120009284, Antimicrobial composition and method for using same; US 20110293757, Compositions comprising tea tree oil and methods for the prevention and treatment of cancer; US 20100273870, Compositions and methods for treating *demodex* infestations; US 20100247376, Antibacterial toothbrush spray; US 20100178284, Composition for the skin, specifically for inhibiting ingrown hair; US 20100173007, Compositions and methods for treating skin conditions in mammals; US 20100056430, Treatment and method for eliminating or reducing foot odor etc.

TTO is known to be active against *Staphylococcus aureus*, including MRSA. TTO is less successful for application in the nose. Also, there is clinical evidence that topical dermatological preparations containing tea tree oil may be more effective than conventional antibiotics in preventing transmission of CA-MRSA. Recent studies support a role for the topical application of TTO in skin care and for the treatment of various diseases and conditions. TTO appears to be effective against bacteria, viruses, fungal infections, mites such as scabies, and lice such as head lice. In the treatment of moderate common acne, topical application of 5% TTO has shown an effect comparable to 5% benzoyl peroxide, albeit with slower onset of action. TTO is a known antifungal agent, effective in vitro against multiple dermatophytes found on the skin. In vivo, shampoo with 5% tea tree oil has been shown to be an effective treatment for dandruff due to its ability to treat *Malassezia* furfur, the most common cause of the condition. One clinical study found that 100% TTO administered topically, combined with debridement, is comparable to clotrimazole in effectiveness against onychomycosis, the most frequent cause of nail disease. The effectiveness of topical tea tree oil preparations for the treatment of the yeast infection Candidiasis is supported by its ability to kill *Candida* in vitro. There is some very limited research that has shown that TTO may have topical antiviral activity, especially against the herpes virus (cold sores), chicken pox, shingles blisters, etc. One study has shown a 5% tea tree oil solution to be more effective than commercial medications against the scabies mite in an in vitro situation.

Nevertheless, despite a remarkable clinical efficiency suggested to TTO, its acute irritation hinders its daily use at high concentrations. Hence, according to the American Cancer Society: "Tea tree oil is toxic when swallowed. It has been reported to cause drowsiness, confusion, hallucinations, coma, unsteadiness, weakness, vomiting, diarrhea, stomach upset, blood cell abnormalities, and severe rashes. It should be kept away from pets and children." A small number of people experience allergic contact dermatitis as a reaction to dermal contact with TTO. In an Italian study of 725 consecutive patients, patients were patch tested with undiluted, 1%, and 0.1% TTO. For undiluted TTO, nearly 6% of the patients observed positive reactions of skin irritation. Only one of 725 patients observed a positive reaction of skin irritation with the 1% dilution. None of the 725 patients observed adverse reactions with the 0.1% dilution. Allergic reactions may be due to the various oxidation products that are formed by exposure of the oil to light and/or air. Moreover, external application of TTO undiluted and/or at inappropriate high doses has been associated with toxicity, including death, in cats and other animals, due to ingestion during grooming. A highly disputed case study reported in The New England Journal of Medicine concluded that repeated topical exposure of lavender and tea tree oils may have caused prepubertal gynecomastia in three young boys, see Henley, Derek V.; Lipson, Natasha; Korach, Kenneth S.; Bloch, Clifford A. (2007). "Prepubertal Gynecomastia Linked to Lavender and Tea Tree Oils". New England Journal of Medicine 356 (5): 479-85. The study involved just three individuals and found lavender to be the only common ingredient used by the boys in the study. While all three cases involved the use of products containing lavender oil as an ingredient, only one boy also used products containing TTO. It was noted that in all cases, the prepubertal gynecomastia reversed after several months. If used in concentrations below 4% or particularly below 0.25%, TTO may fail to kill bacteria and create selection pressure, which may result in them becoming less sensitive to tea tree oil and even some antibiotics in vitro. Undiluted tea tree oil can cause some hearing loss when used in the ears of animals; however, a 2% concentration has not been shown to have any lasting effect. It is not known whether the same is true for humans.

Hence, as one can see TTO efficiency in treating skin conditions increases from above approximately 0.25%, whilst its irritation is found concentration greater than 0.1%.

Skin treatment by hypertonic solutions and compositions thereof are known in the art. As an example, WO/2009/125383, A MEDICAL COVERING FOR HEALING WOUNDS AND SKIN DISEASES, which is incorporated herein as a reference, discloses a medical covering used for dermatological diseases and topical pathogeneses. The range of this treatment and the time required for achieving a complete cure is moderate.

Use of honey in the cosmetic industry in known in the art. Hence for example, U.S. Pat. No. 5,965,145 discloses use of 0.1 to 10 weight percent honey as keratolytic agent for improving the radiance and the complexion of the skin and treating wrinkles U.S. Pat. No. 5,017,367 discloses a cosmetic composition wherein honey present is in an amount between 0.005 to 0.01 parts per 1 part carrier medium. U.S. Pat. No. 6,551,606 discloses a cosmetic product that contains enzymes and has an intensive skin action, especially a regenerative effect The inventive cosmetic product contains 0.01 to 5 wt. % of a concentrate of the coconut milk of Cocos nucifera, containing peroxidase, lipase and protease; 0.1 to 10 wt. % of a plant milkwater, and 0.01 to 5 wt. % of a glycerol extract of a mixture consisting of honey, rice hulls, rice hull oil and/or rice germ oil; with the remainder consisting of cosmetic auxiliary agents, active agents and carrier substances.

The use of honey and its alternatives in combination with TTO was rarely discussed. U.S. Pat. No. 5,738,863 "Honey bee repellent composition comprising tea tree oil" discloses a social stinging insect repellent composition comprises effective repelling amounts of tea tree oil and benzaldehyde. U.S. Pat. No. 7,147,876 "Compositions for removal of toxins" discloses a medicinal or cosmetic composition comprising Aloe vera in combination with at least one vitamin, a minerals concentrate, an organic oils concentrate, at least one Chinese Herb, at least one essential oil and at least one spice. The invention shows, in one of its embodiments, that the Aloe vera-based composition may also comprise a honey product such as royal jelly or bee propolis. US20110135746 "Protective lip balm composition" discloses a lip balm formulations which comprise a combination of anti-bacterial, anti-viral, and anti-fungal substances, including: bees wax, cocoa butter, Shea butter, Jojoba oil, Naroli oil, myrrh, tea tree oil, lavender oil, Blue Moroccan chamomile, and vitamin E and, optionally, Manuca honey and Aloe vera either singularly or together with the other ingredients.

Hence, a cost effective non skin irritating TTO-based therapeutic composition useful for cosmetics and both veterinary and human medicine which is characterized by a wide spectrum of effective biocidic and dermal action and yet is generally regarded as safe and non-irritant is still a long felt need.

SUMMARY OF THE INVENTION

It is thereby provided here a cost effective TTO-based therapeutic composition of synergistic effect. The hereby disclosed high load TTO-containing composition useful for both veterinary and human medicine which is (i) characterized by a wide spectrum of action and high efficiency and yet (ii) is generally regarded as safe and non-irritant.

According to one embodiment of the invention, said composition comprises (i) a TTO, 0.05 to 0.75% (wt/wt); and (ii) at least one hypertonic composition providing the composition to 1700 to 2500 mOsm/L, 10 to 60% (wt/wt) and inorganic salts, 0.01% to 0.5% (wt/wt). The compositions herein and below may comprise magnesium sulfate up to about 0.5% (wt/wt).

According to yet another embodiment of the invention, the composition herein and below comprising an effective measure (e.g., 0.1 to 3%) of one or more water immiscible ingredients, solvents, co-solvents and diluents, selected from a group consisting inter alia of olive oil, hash oil, Sea Buckthorn Berry (Obliphica) oil, lavender oil, any suitable vegetable or seed oil, and any mixture thereof. According to yet another embodiment of the invention, the composition herein and below is diluted, dissolved, homogenized or dispersed within a hypertonic emulsion. According to yet another embodiment of the invention, the composition herein and below is diluted, dissolved, homogenized or dispersed in a salt-based hypertonic solution, wherein said hypertonic solution or emulsion comprises polysaccharides or not.

According to yet another embodiment of the invention, said composition comprises TTO, 0.25% (wt/wt); at least one type of sugar, such as dextrose, in a concentration to form 1725 mOsm/L or more, and one or more inorganic salts selected from a group consisting zinc picolinate, zinc oxalate, zinc oxide; copper sulfate, copper bisulfate; copper oxide up to about 0.02% (each, wt/wt) (Synergic Composition No. 1).

According to yet another embodiment of the invention, said composition comprises TTO, 0.50% (wt/wt); dextrose in a concentration to form 1725 mOsm/L or more, and one or more inorganic salts selected from a group consisting zinc picolinate, zinc oxalate, zinc oxide; copper sulfate, copper bisulfate; copper oxide up to about 0.02% (each, wt/wt) (Synergic Composition No. 2).

According to yet another embodiment of the invention, said composition comprises TTO, 0.75% (wt/wt); dextrose in a concentration to form 1725 mOsm/L or more, and one or more inorganic salts selected from a group consisting zinc picolinate, zinc oxalate, zinc oxide; copper sulfate, copper bisulfate; copper oxide up to about 0.02% (each, wt/wt) (Synergic Composition No. 3).

According to yet another embodiment of the invention, said composition comprises TTO, 1.0% (wt/wt); dextrose in a concentration to form 1725 mOsm/L or more, 10 to 60% (wt/wt) and one or more inorganic salts selected from a group consisting zinc picolinate, zinc oxalate, zinc oxide; copper sulfate, copper bisulfate; copper oxide up to about 0.02% (each, wt/wt) (Synergic Composition No. 4).

According to yet another embodiment of the invention, said composition comprises TTO, 0.5% (wt/wt); at least one type of sugar, such as dextrose, in a concentration to form 2200 mOsm/L or more, and one or more inorganic salts selected from a group consisting zinc picolinate, zinc oxalate, zinc oxide; copper sulfate, copper bisulfate; copper oxide up to about 0.02% (each, wt/wt) (Synergic Composition No. 5).

According to yet another embodiment of the invention, said composition comprises TTO, 0.5% (wt/wt); at least one type of sugar, such as dextrose, in a concentration to form 2550 mOsm/L or more, and one or more inorganic salts selected from a group consisting zinc picolinate, zinc oxalate, zinc oxide; copper sulfate, copper bisulfate; copper oxide up to about 0.02% (each, wt/wt) (Synergic Composition No. 6).

According to yet another embodiment of the invention, said composition comprises TTO, 0.5% (wt/wt); Mono-(corn originated)-poly saccharide in a concentration to form 2000 mOsm/L, and one or more inorganic salts selected from a group consisting zinc picolinate, zinc oxalate, zinc oxide; copper sulfate, copper bisulfate; copper oxide up to about 0.02% (each, wt/wt) (Synergic Composition No. 7).

According to yet another embodiment of the invention, said composition comprises TTO, 0.5% (wt/wt); Mono-(corn originated)-poly saccharide in a concentration to form 2000 mOsm/L, and Dead Sea salts, 0.01 to 1.00% (wt/wt) (Synergic Composition No. 8). Dead Sea salts may comprise, inter alia, Silicon dioxide, Calcium oxide, Aluminum oxide, Magnesium oxide, Iron(III) oxide, Sodium oxide, Potassium oxide, Titanium(IV) oxide, Sulfur trioxide, Phosphorus pentoxide, Chlorides and Bromides.

According to yet another embodiment of the invention, said composition comprises TTO, 0.5% (wt/wt); Mono-(corn originated)-poly saccharide in a concentration to form 2000 mOsm/L, and inorganic salts selected from a first group consisting of one zinc picolinate, zinc oxalate, zinc oxide; copper sulfate, copper bisulfate; copper oxide at 0.02% (each, wt/wt); and Dead Sea salts, 0.01 to 1.00% (wt/wt) (Synergic Composition No. 9).

According to yet another embodiment of the invention, said composition comprises TTO, 0.5% (wt/wt); hypertonic solution saline, from 7.5% to 9%, and inorganic salts selected from a first group consisting of one zinc picolinate, zinc oxalate, zinc oxide; copper sulfate, copper bisulfate; copper oxide up to about 0.5% (each, wt/wt); and Dead Sea salts, 0.01 to 1.00% (wt/wt) (Synergic Composition No. 10).

According to yet another embodiment of the invention, said composition comprises TTO, 0.5% (wt/wt); untreated commercially available bee's honey, from 7.5% to 12%, and inorganic salts selected from a first group consisting of one zinc picolinate, zinc oxalate, zinc oxide; copper sulfate, copper bisulfate; copper oxide up to about 0.5% (each, wt/wt); and Dead Sea salts, 0.01 to 1.00% (wt/wt) (Synergic Composition No. 11).

According to yet another embodiment of the invention, said composition comprises TTO, 0.5% (wt/wt); Dead Sea salts to form 2500 mOms/L, e.g., commercially available by AHAVA Ltd (IL) Dead Sea Liquid Salt (Synergic Composition No. 12).

According to yet another embodiment of the invention, said composition comprises additionally comprising at least one additive.

According to yet another embodiment of the invention, a method producing a non-irritating tea tree oil (TTO)-based topical therapeutic composition is disclosed. The said method comprises at least one step of admixing TTO, 0.05 to 1.0% (wt/wt); at least one hypertonic composition, 10 to 60% (wt/wt); and inorganic salts, 0.01% to 1.0% (wt/wt) such as a homogonous composition of 1700 to 2500 mOsm/L is obtained.

According to yet another embodiment of the invention, a method of treating dermatology conditions in mammals is further disclosed. The method comprises steps of (a) admixing TTO, 0.05 to 1.0% (wt/wt); at least one hypertonic composition, 10 to 60% (wt/wt); and inorganic salts, 0.01% to 1.0% (wt/wt) such as a homogonous composition of 1700 to 2500 mOsm/L is obtained; and (b), applying said homogonous composition directly on skin to be treated; said method is characterized by an effective, rapid & wide spectrum of action whilst being non-irritant to patient skin.

It is thus in the scope of the invention wherein the dermatology conditions in mammals are selected in a non-limiting manner from allergies and skin allergies, skin atopy and atopy dermatitis, psoriasis. Acne wrinkles Dry skin, skin irritations, Rosacea, dermatitis and general relief.

BRIEF DESCRIPTION OF THE DRAWINGS

The subject matter regarded as the invention will become more clearly understood in light of the ensuing description of embodiments herein, given by way of example and for purposes of illustrative discussion of the present invention only, with reference to the accompanying photographs, wherein.

DETAILED DESCRIPTION OF THE PREFERRED EMBODIMENTS

Figure 1:
FIG. 1 is a photo of Gidi, a young dog with *Aspergillums* infected and filtrating nostril (before treatment)
Figure 2:
FIG. 2 is a photo of Gidi after traditional treatment by Itraconazole.
Figure 3:
FIG. 3 is a photo of Gidi after treatment comprising, inter alia, topical application of Synergic Composition No. 1.
Figure 4:
FIG. 4 is a photo of dog Petel with chronic skin bacteria and yeast infections, before treatment.
Figure 5:
FIG. 5 is a photo of Petel after treatment by Synergic Composition No. 3.
Figure 6A:
FIGS. 6a and 6b are photos of Dog 'Petel', rear leg, with sever Canine *Staphylococcal* Pyoderma before treatment.
Figure 6B:
Figure 7:
FIG. 7 is a photo of Petel after treatment by Synergic Composition No. 5.
Figure 8:
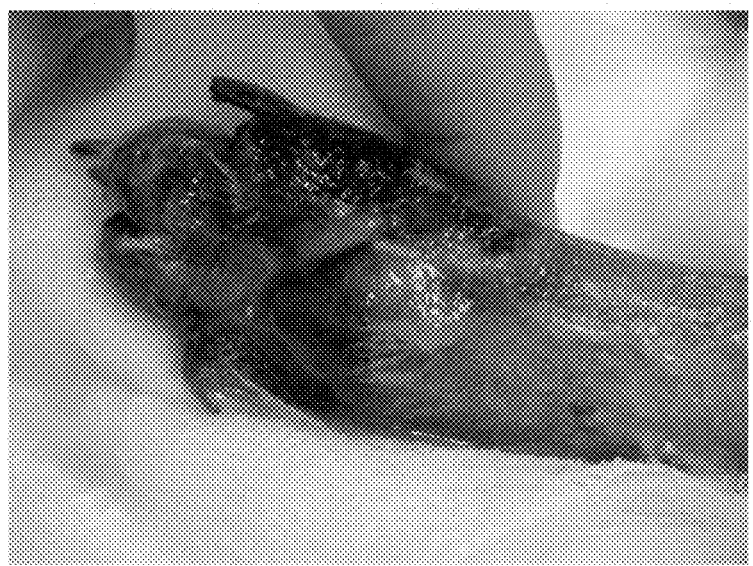
FIG. 8 is a photo of untreated dog 'Emi', with a severe necrosis in its left rear leg caused by an accidental injury.
Figure 9A:
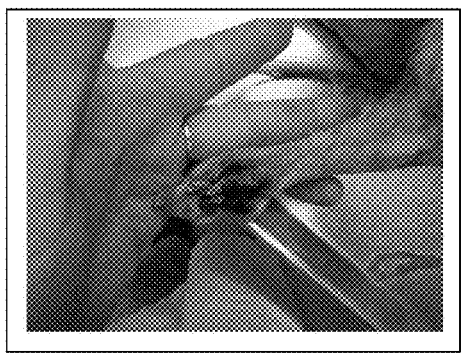
FIGS. 9a and 9b are photos of 'Petel' after treatment by Synergic Composition No. 10.
Figure 9B:
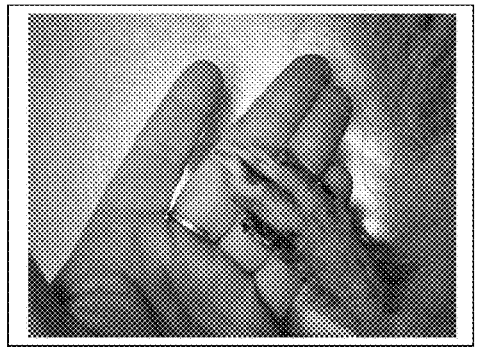
Figure 10:
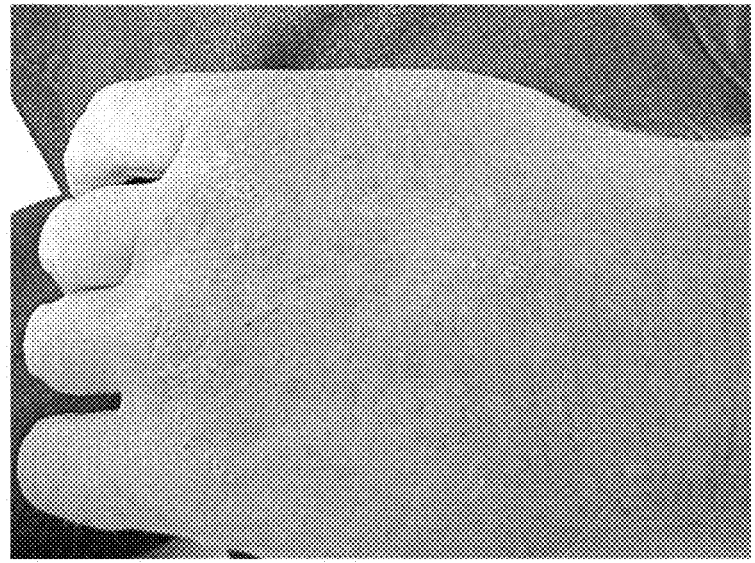
FIG. 10 is a photo of a right hand of a human patient 'R' before treatment.
Figure 11:
FIG. 11 is a photo shows the same hand after seven day of treatment by Synergic Compositions No. 11.
Figure 12A:
FIGS. 12a and 12b are photos of 'Lola' before and after treatment by Synergic Composition No. 28.
Figure 12B:

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a hypertonic TTO-based therapeutic composition of synergistic effect and methods thereof is disclosed.

It is thereby provided here a cost effective hypertonic TTO-based therapeutic composition of synergistic effect. The hereby disclosed high load TTO-containing composition useful for both veterinary and human medicine which is (i) characterized by a wide spectrum of action and high efficiency and yet (ii) is generally regarded as safe and non-irritant. It is thus well within the scope of the invention, wherein said composition comprises (i) a TTO, 0.05 to 0.75% (wt/wt); and (ii) at least one hypertonic composition providing the composition to 1700 to 2500 mOsm/L, 10 to 60% (wt/wt) and inorganic salts, 0.01% to 0.5% (wt/wt).

It is in the scope of the invention wherein the TTO-based non-irritating compositions further comprising zinc salts and cupper salts, such as (i) zinc and cupper gluconate, and/or (ii) calamine, namely either a mixture of zinc oxide (ZnO) with about 0.5% ferric oxide ($Fe_2O_3$) or a zinc carbonate compound.

It is well in the scope of the invention wherein the TTO-based non-irritating compositions are provided as a topical cosmetics and medications which are selected, in a non-limiting manner, for balms, creams, gels, oils, lotions, patches, ointments, soap-like or shampoo-like compositions and other products that are apply to skin. The said topical cosmetics and medications are either homogenous or heterogeneous. Emulsions, such micro-emulsions, water in oil emulsions, oil in water emulsions and double emulsions and liposomal (MLV, SLV, nano-emulsions) compositions are possible. Oil containing topical cosmetics and medications are also in the scope of the invention, wherein said oils are selected, in a non-limiting manner, from fish oil, omega three fatty acids and oils, cannabis oil, Oblepicha oil, Sea-Buckthorn oil, mineral oil, plant seeds oil, eucalyptus oil, lavender oil, olive tree oil and water immiscible plant extracts are possible oils to be used. Topical cosmetics and medications as defined hereinafter may comprise inorganic salts such as Dead Sea salts.

The term 'cosmetics' refers hereinafter in a non limiting manner to various skin-care creams, lotions, powders, perfumes, lipsticks, fingernail and toe nail polish, eye and facial makeup, towelettes, permanent waves, colored contact lenses, hair colors, hair sprays and gels, deodorants, hand sanitizer, baby products, bath oils, bubble baths, bath salts, butters and many other types of products.

It is in the scope of the invention wherein the compositions defined and claimed are useful for treating dermatological conditions, such as pathological conditions, chronic dermal problems and age related dermal conditions which may include in a non limiting manner acne, pyoderma, chronic skin irritation, atopic dermatitis or dermatitis as general bites, skin related inflammatory conditions and GI-related IBD, autoimmune diseases, hyper keratosis, Psoriasis, Burns caused by chemical, radiation, or physical reasons, hemorrhoid and fissure, dry skin condition, old age dermal condition, or wrinkles age related conditions. The compositions defined and claimed are also useful for treating Herpes virus including herpes zoster, infectious mononucleosis, pox virus, foot-and-mouth disease, foot-hand-and-mouth disease.

The terms 'hypertonic' and 'hyperosmotic' interchangeably refer to any topical cosmetics and medications which has a higher concentration of solutes than the cells with which it is in contact, so that water is drawn out of the cells and into the solution by osmosis. The terms are especially useful to hypertonic compositions characterized by about 1700 to about 2,500 mOsm/L.

The term 'additives' refers hereinafter to either organic (natural occurring or synthesized materials) or inorganic compositions, in a fluid, gas or solid state, selected in a non-limiting manner form a group consisting, inter alia, of biocides, medicaments, narcotics, pain-relieving agents, oils and oils as described above, heparin and heparin-like agents, anticoagulants or coagulation factors, pharmaceuticals, binders, pigments, emulsifiers or soaps, de-emulsifiers, solvents, oils, plant extracts, essential oils, perfumes, sustain released drugs, markers, biomarkers, electrolytes, inorganic salts and compositions thereof, such as calamine, enzymes, hormones, proteins, vitamins, nutrients, hash oil, or any combination thereof.

The term 'carrier' refers to any fluid that is characterized by being able to withdraw water from living cells, said fluid being in any appropriate form, including but not limited to liquids, solutions (whether water-miscible or water-immiscible), organic solvents, suspensions, dispersions, emulsions, fluid polymers, finely divided solids, nano-particles, microparticles, powders, fine powders, gases, gels, aerosols, supercritical fluids, ionic liquids, surfactants, liposomes or any combination thereof. According an embodiment of the invention, the term 'salts' refers, in a non-limiting manner, to one or more compositions that are selected in a non-limiting manner from one or more compositions selected from a group consisting, inter alia, of one or more cations and elements, such as sodium, potassium, boron, silica, magnesium, calcium, zinc, copper, ferrous silver pt gold; and one or more anions, such as chlorides, hydroxides, phosphates or ammonium; or any combination thereof. The term 'sugars' refers to one or more of four chemical groupings of carbohydrates: monosaccharide, disaccharide, oligosaccharide, and polysaccharide. The term 'honey' refers to any natural occurring honey, or honey-like synthesized compositions, such as compositions comprise ingredients as follows e.g., fructose: about 38.0%, glucose: about 31.0%, sucrose: about 1.0%, water: about 17.0%, other sugars: about 9.0% (maltose, melezitose), ash: about 0.17% and additives: about 3.38% (weight percent). The term 'hydrogels' refers to any composition adapted to comprise more than 98% water. It is one embodiment of the invention wherein cationic polymers are utilized, such as copolymers of vinylpyrrolidone, methacrylamide, and N-vinylimidazole. It is another embodiment of the invention wherein Poly ethylene glycol (PEGs) familyare utilized. The family comprises, inter alia, PEG, polyethylene oxides (PEOs) or polyoxyethylenes (POEs) etc.

The term 'about' refers hereinafter to ±20% of the defined measure.

According an embodiment of the invention, sugars (i.e., any mono-saccharides, disaccharides or complex carbohydrates) are selected in a non-limiting manner from one or more compositions selected from a group consisting, inter alia, mono-saccharides comprising aldoses and ketoses having a number of about 3 to about carbon atoms per molecule, such as triose (e.g., aldotriose such as glyceraldehyde or ketotriose such as dihydroxyacetone); tetraose (e.g., erythrose and threose, or; pentose (e.g., arabinose, lyxose, ribose and xylose or ribulose and; hexose (e.g., allose, altrose, galactose, glucose (i.e., dextrose), gulose, idose, mannose and talose, or fructose, psicose, sorbose and tagatose) etc. A combination of all said sugars is well in the scope of the invention. Examples of disaccharides are provided in a non-limiting manner: sucrose, lactose, maltose, trehalose, cellobiose etc.

Oligosaccharides are saccharide polymers containing a small number (e.g., three to ten) of component sugars, also known as simple sugars, e.g., Fructo-oligosaccharides etc. Polysaccharides are selected from homo-poly-saccharides and het-ero-poly-saccharides, especially those selected from a group consisting, inter alia, of alginates, carrageenan, chitin, ficoll, fructans, galactans, glucans, glycosaminoglycans, mannans, pectins, pentosan sulfuric polyester, plant Gums, bacterial polysaccharides, proteoglycans, sepharose, xylane, gum guar, and any combination and mixtures thereof.

Reference is now made to image 1, showing 'Gidi', a young dog with *Aspergillums* infected and filtrating nostril (before treatment). The nostril is very sensitive. Veterinary care is difficult in this very sensitive location.

Reference is now made to image 2. Traditional treatment by Itraconazole (commercially available Sporanox, 50 mg, 2 times per day) fails. The nostril is still infected and very sensitive. At this stage a combined treatment incorporating (i) Itraconazole treatment (13 mg, 2 times per day); and (ii) topical applying Synergic Composition No. 1 (2 times per day) started.

Reference is now made to image 3. After one week, the combined treatment cured the infection. The nostril gain its pigmentation, pain was over and *Aspergillums* infection was completely controlled.

Synergic Compositions No. 1 to 12 similarly demonstrate a very good therapeutically activity against various in vivo or in vitro fungal infections, including Tinea versicolor, Cutaneous mycoses caused by *Microsporum*, and *Epidermophyton* fungi, *Cryptococcus* species *Candida* species *Aspergillus* species *Histoplasma capsulatum* etc.

One years old dog ('Petel') has chronic skin infections. Reference is now made to image 4, showing a sever nail (front leg) infection by bacteria and yeast. This deep infection was wildly spread at sinus unguis, radix unguis, eponychium, and nail bed. The nail and nail's surroundings were irritant and pain.

Reference is now made to image 5. The infected nail was treated by Synergic Composition No. 3 (the composition was applied directly on tissue, two times per day, 3 days). Reference is now made to image 5, showing a complete cure after 3 days of treatment.

Reference is now made to images 6a and 6b, showing Dog 'Petel', rear leg, with sever Canine *Staphylococcal* Pyoderma. The infected tissue is very sensitive to touch, and characterized by intensive inflammation, pus producing abscess.

Reference is now made to image 7, showing Petel's rear leg after two weeks of treatment by Synergic Composition No. 5 (two times per day). Synergic Composition No. 5 was applied directly on the infected sensitive tissue. No pain or remarkable sensitivity was detected whilst applying said TTO-rich composition.

Reference is now made to image 8, showing dog 'Emi'. Emi has untreated a sever necrosis in its left rear leg caused by an accidental injury. Blood flow in this leg is highly limited. The leg is necrotic and can-not bear weight. Reference is now made to image 9, showing 'Emi' after 4 day of treatment by Synergic Compositions No. 10 (four times per day). Synergic Composition No. 10 was applied directly on the necrotic organ. No pain or remarkable sensitivity was detected whilst applying said TTO-rich composition.

Reference is now made to image 10, showing a right hand of a human patient 'R', a Caucasian male (52). R has untreated, chronic itching and irritate pathologic skin condition. Reference is now made to image 11, showing the same hand after seven day of treatment by Synergic Compositions No. 11 (two times per day). Synergic Composition No. 11 was applied directly on the sick skin and completely treated the skin after a protocol of about 14 days. No pain or remarkable sensitivity was detected whilst applying said TTO-rich composition.

According to yet another embodiment of the invention, provided here in a non limiting manner a non-irritating TTO-based topical therapeutic synergic composition (Synergic Composition No. 13) which comprises ingredients as follows:

| % | FUNCTION | CAS | INCI/CTFA Name |
|---|---|---|---|
| 50.000 | | 492-62-6/921-60-8 | Dextrose |
| 41.000 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.500 | Anti-Bacterial | 68647-73-4 | Tea Tree Oil |
| 0.100 | Preservative | 532-32-1 | Sodium Benzoate |
| 0.300 | | 527-09-3 | Copper Gluconate |
| 1.000 | | 527-09-3 | Magnesium Sulfate |
| 0.300 | | 4468.02.4 | Zinc Gluconate/OXIDE |
| 100.000 | | | |

According to yet another embodiment of the invention provided here in a non limiting manner a non-irritating TTO-based topical therapeutic synergic composition (Synergic Composition No. 14) which comprises ingredients as follows:

| % | FUNCTION | CAS | INCI/CTFA Name |
|---|---|---|---|
| 50.000 | | 492-62-6/921-60-8 | Dextrose |
| 42.270 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.500 | Anti-Bacterial | 68647-73-4 | Tea Tree Oil |
| 0.100 | Preservative | 532-32-1 | Sodium Benzoate |
| 0.300 | | 527-09-3 | Magnesium Sulfate |
| 0.030 | | 4468.02.4 | Zinc Gluconate/Oxide |
| 100.000 | | | |

According to yet another embodiment of the invention provided here in a non limiting manner a non-irritating TTO-based topical therapeutic synergic composition (Synergic Composition No. 15) which comprises ingredients as follows:

| % | FUNCTION | CAS | INCI/CTFA Name |
|---|---|---|---|
| 50.000 | | 492-62-6/921-60-8 | Dextrose |
| 42.540 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.500 | Anti-Bacterial | 68647-73-4 | Tea Tree Oil |
| 0.100 | Preservative | 532-32-1 | Sodium Benzoate |
| 0.030 | | 527-09-3 | Copper Gluconate |
| 0.030 | | 4468.02.4 | Zinc Gluconate/Oxide |
| 100.000 | | | |

According to yet another embodiment of the invention, provided here in a non limiting manner a non-irritating TTO-based topical therapeutic synergic composition (Synergic Composition No. 16) which comprises ingredients as follows:

| % | FUNCTION | CAS | INCI/CTFA Name |
|---|---|---|---|
| 30.000 | | 492-62-6/921-60-8 | Dextrose |
| 62.540 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.500 | Anti-Bacterial | 68647-73-4 | Tea Tree Oil |
| 0.100 | Preservative | 532-32-1 | Sodium Benzoate |
| 0.030 | | 527-09-3 | Copper Gluconate |
| 0.030 | | 4468.02.4 | Zinc Gluconate/Oxide |
| 100.000 | | | |

According to yet another embodiment of the invention provided here in a non limiting manner a non-irritating TTO-based topical therapeutic synergic composition (Synergic Composition No. 17) which comprises ingredients as follows:

| % | FUNCTION | CAS | INCI/CTFA Name |
|---|---|---|---|
| 70.000 | | 492-62-6/921-60-8 | Dextrose |
| 22.540 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.500 | Anti-Bacterial | 68647-73-4 | Tea Tree Oil |
| 0.100 | Preservative | 532-32-1 | Sodium Benzoate |
| 0.030 | | 527-09-3 | Copper Gluconate |
| 0.030 | | 4468.02.4 | Zinc Gluconate/Oxide |
| 100.000 | | | |

According to yet another embodiment of the invention provided here in a non limiting manner a non-irritating TTO-based topical therapeutic synergic composition (Synergic Composition No. 18) which comprises ingredients as follows:

| % | FUNCTION | CAS/IUPAC | INCI/CTFA Name |
|---|---|---|---|
| 50.000 | | 492-62-6/921-60-8 | Dextrose |
| 37.270 | Moisturizer | 7789-20-0 | Aqua |
| 5.000 | Humectant | 56-81-5 | Glycerin |
| 0.600 | Thickening | 11138-66-2 | Xanthan Gum |

-continued

| % | FUNCTION | CAS/IUPAC | INCI/CTFA Name |
|---|---|---|---|
| 0.600 | Thickening | 9004-62-0 | Hydroxyethylcellulose |
| 0.600 | Preservative | | Phenoxyethanol & Caprylyl Glycol & Chlorphenesin |
| 0.500 | Anti-Bacterial | 68647-73-4 | Tea Tree Oil |
| 5.000 | local anesthetic & antiarrhythmic drug | 137-58-6/94-09-7 | Lidocaine/benzocaine |
| 0.100 | Preservative | 532-32-1 | Sodium Benzoate |
| 0.300 | | 527-09-3 | Magnesium Sulfate |
| 0.030 | | 4468.02.4 | Zinc Gluconate/Oxide |
| 100.000 | | | |

According to yet another embodiment of the invention provided here in a non limiting manner a non-irritating TTO-based topical therapeutic synergic composition (Synergic Composition No. 19) which comprises ingredients as follows:

| % | FUNCTION | CAS/IUPAC | INCI/CTFA Name |
|---|---|---|---|
| 50.000 | | 492-62-6/921-60-8 | Dextrose |
| 37.270 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.500 | Anti-Bacterial | 68647-73-4 | Tea Tree Oil |
| 5.000 | antiseptic | 10043-35-3 | Boric acid |
| 0.100 | Preservative | 532-32-1 | Sodium Benzoate |
| 0.300 | | 527-09-3 | Magnesium Sulfate |
| 0.030 | | 4468.02.4 | Zinc Gluconate/Oxide |
| 100.000 | | | |

According to yet another embodiment of the invention provided here in a non limiting manner a non-irritating TTO-based topical therapeutic synergic composition (Synergic Composition No. 20) which comprises ingredients as follows:

| % | FUNCTION | CAS/IUPAC | INCI/CTFA Name |
|---|---|---|---|
| 50.000 | | 492-62-6/921-60-8 | Dextrose |
| 42.270 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.500 | Anti-Bacterial | 68647-73-4 | Tea Tree Oil |
| 0.100 | Preservative | 532-32-1 | Sodium Benzoate |
| 0.300 | | 527-09-3 | Magnesium Sulfate |
| 0.030 | | 1314-13-2 | Zinc oxide |
| 100.000 | | | |

According to yet another embodiment of the invention, provided here in a non limiting manner a non-irritating TTO-based topical therapeutic synergic composition (Synergic Composition No. 21) which comprises ingredients as follows, to treat e.g., Pruritus:

| % | FUNCTION | CAS | INCI/CTFA Name |
|---|---|---|---|
| 30.000 | | 492-62-6/921-60-8 | Dextrose |
| 62.440 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.500 | Anti-Bacterial | 68647-73-4 | Tea Tree Oil |
| 0.100 | Preservative | 532-32-1 | Sodium Benzoate |
| 0.100 | | 144-55-8 | Sodium Bicarbonate |
| 0.030 | | 527-09-3 | Copper Gluconate |
| 0.030 | | 4468.02.4 | Zinc Gluconate/Oxide |
| 100.000 | | | |

According to yet another embodiment of the invention provided here in a non limiting manner a non-irritating TTO-based topical therapeutic synergic composition (Synergic Composition No. 22) which comprises ingredients as follows:

| % | FUNCTION | CAS/IUPAC | INCI/CTFA Name |
|---|---|---|---|
| 50.000 | | 492-62-6/921-60-8 | Dextrose |
| 40.770 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 1.000 | Anti-Bacterial | 68647-73-4 | Tea Tree Oil |
| 0.100 | Preservative | 532-32-1 | Sodium Benzoate |
| 0.300 | | 527-09-3 | Magnesium Sulfate |
| 0.030 | | 1314-13-2 | Zinc oxide |
| 100.000 | | | |

According to yet another embodiment of the invention provided here in a non limiting manner a non-irritating TTO-based topical therapeutic synergic composition (Synergic Composition No. 23) which comprises ingredients as follows:

| % | FUNCTION | CAS/IUPAC | INCI/CTFA Name |
|---|---|---|---|
| 50.000 | | 492-62-6/921-60-8 | Dextrose |
| 40.770 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 2.000 | Anti-Bacterial | 68647-73-4 | Tea Tree Oil |
| 0.100 | Preservative | 532-32-1 | Sodium Benzoate |
| 0.300 | | 527-09-3 | Magnesium Sulfate |
| 0.030 | | 1314-13-2 | Zinc oxide |
| 100.000 | | | |

According to yet another embodiment of the invention provided here in a non limiting manner a non-irritating TTO-based topical therapeutic synergic composition (Synergic Composition No. 24) which comprises ingredients as follows:

| % | FUNCTION | CAS/IUPAC | INCI/CTFA Name |
|---|---|---|---|
| 50.000 | | 492-62-6/921-60-8 | Dextrose |
| 42.720 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.050 | Anti-Bacterial | 68647-73-4 | Tea Tree Oil |
| 0.100 | Preservative | 532-32-1 | Sodium Benzoate |
| 0.300 | | 527-09-3 | Magnesium Sulfate |
| 0.030 | | 1314-13-2/ 17949-65-4 | Zinc oxide/picolinate |
| 100.000 | | | |

According to yet another embodiment of the invention provided here in a non limiting manner a non-irritating TTO-based topical therapeutic synergic composition (Synergic Composition No. 25) which comprises ingredients as follows:

| % | FUNCTION | CAS/IUPAC | INCI/CTFA Name |
|---|---|---|---|
| 50.000 | | 492-62-6/921-60-8 | Dextrose |
| 37.720 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.050 | Anti-Bacterial | 68647-73-4 | Tea Tree Oil |
| 0.100 | Preservative | 532-32-1 | Sodium Benzoate |
| 5.300 | | 527-09-3 | Magnesium Sulfate |
| 0.030 | | 1314-13-2/17949-65-4 | Zinc oxide/picolinate |
| 100.000 | | | |

According to yet another embodiment of the invention, provided here in a non limiting manner a non-irritating TTO-based topical therapeutic synergic composition (Synergic Composition No. 26) which comprises ingredients as follows for treating psoriatic vestibulitis and dry skin conditions, which is composed as follows:

| % | FUNCTION | CAS/IUPAC | INCI/CTFA Name |
|---|---|---|---|
| 50.000 | | 492-62-6/921-60-8 | Dextrose |
| 32.720 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.050 | Anti-Bacterial | 68647-73-4 | Tea Tree Oil |
| 0.100 | Preservative | 532-32-1 | Sodium Benzoate |
| 10.300 | | 527-09-3 | Magnesium Sulfate |
| 0.030 | | 1314-13-2/17949-65-4 | Zinc oxide/picolinate |
| 100.000 | | | |

According to yet another embodiment of the invention provided here in a non limiting manner a non-irritating TTO-based topical therapeutic synergic composition (Synergic Composition No. 27) which comprises ingredients as follows:

| % | FUNCTION | CAS | INCI/CTFA Name |
|---|---|---|---|
| 50.000 | | 492-62-6/921-60-8 | Dextrose |
| 40.900 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.500 | Anti-Bacterial | 68647-73-4 | Tea Tree Oil |
| 0.100 | Preservative | 532-32-1 | Sodium Benzoate |
| 0.100 | 8002-09-3 | | Hash oil (Cannabis oil) |
| 0.300 | | 527-09-3 | Copper Gluconate |
| 1.000 | | 527-09-3 | Magnesium Sulfate |
| 0.300 | | 4468.02.4 | Zinc Gluconate |
| 100.000 | | | |

Reference is now made to image 8, showing dog 'Lola' before and after treatment by Synergic Composition No. 28. According to yet another embodiment of the invention, provided here in a non limiting manner a non-irritating TTO-based topical therapeutic synergic composition (Synergic Composition No. 28) which comprises ingredients as follows:

| % | FUNCTION | CAS | INCI/CTFA Name |
|---|---|---|---|
| 50.000 | | 492-62-6/921-60-8 | Dextrose |
| 38.500 | Moisturizer | 7789-20-0 | Aqua |
| 5.000 | Humectant | 56-81-5 | Glycerin |
| 0.600 | Thickening | 11138-66-2 | Xanthan Gum |
| 0.600 | Thickening | 9004-62-0 | Hydroxyethylcellulose |
| 0.600 | Preservative | | Phenoxyethanol & Caprylyl Glycol & Chlorphenesin |
| 0.500 | Anti-Bacterial | 68647-73-4 | Tea Tree Oil |
| 0.100 | Preservative | 532-32-1 | Sodium Benzoate |
| 2.500 | 8002-09-3 | | Dead sea salts* |
| 0.300 | | 527-09-3 | Copper Gluconate |
| 1.000 | | 527-09-3 | Magnesium Sulfate |
| 0.300 | | 4468.02.4 | Zinc Gluconate |
| 100.000 | | | |

Synergic Compositions No. 1 to 28 similarly demonstrate a very good therapeutically activity against various in vivo or in vitro bacterial infections, *Staphylococcus* and *Streptococcus* species; *Pseudomonas aeruginosa*; *Burkholderia cenocepacia*, and *Mycobacterium avium*; *Mycobacterium* and *Brucella Bordetella* pertussis, *Borrelia burgdorferi*, *Brucella abortus*; *Brucella canis*; *Brucella melitensis*; *Brucella suis*; *Campylobacter jejuni*; *Chlamydia pneumoniae*; *Chlamydia trachomatis*; *Chlamydophila psittaci*; *Clostridium botulinum*; *Clostridium difficile*; *Clostridium perfringens*; *Clostridium tetani*; *Corynebacterium diphtheriae*; *Enterococcus faecalis*, *Enterococcus faecium*; *Escherichia coli*; *Francisella tularensis*; *Haemophilus influenzae*; *Helicobacter pylori*; *Legionella pneumophila*; *Listeria monocytogenes*; *Mycobacterium leprae*; *Mycobacterium tuberculosis*; *Mycobacterium ulcerans*, *Pseudomonas aeruginosa*, *Staphylococcus aureus*; *Staphylococcus epidermidis*, *Staphylococcus saprophyticus*, *Streptococcus agalactiae*, *Streptococcus pneumoniae*, *Streptococcus pyogenes*, and *Propionibacterium acnes*.

Synergic Compositions No. 1 to 28 similarly demonstrate a good therapeutically activity against various in vivo or in vitro viral infections, DNA-type virus RNA type virus both of which are obligatory intracellular parasites.

Synergic Compositions No. 1 to 28 similarly demonstrate an excellent therapeutically activity against various in vivo or in vitro parasitic infestations, stings, and bites, as those caused by the following phyla: Annelida, Arthropoda, Bryozoa, Chordata, Cnidaria, Cyanobacteria, Echinodermata, Nemathelminthes, Platyhelminthes, and Protozoa.

Synergic Compositions No. 1 to 28 similarly demonstrate an effective therapeutically activity against autoimmune dermal inflammation, such as Scleroderma and psoriasis.

The invention claimed is:

1. A non-irritating tea tree oil (TTO)-based topical therapeutic composition useful for both veterinary and human dermatology comprising a homogeneous mixture of:
   a. TTO, 0.5% (wt/wt);
   b. at least one hypertonic composition; and
   c. inorganic salts consisting of a mixture of copper gluconate provided in 0.03% (wt/wt) and either zinc gluconate or zinc oxide provided in 0.03% (wt/wt),
   characterized by an effective, rapid and wide spectrum of action whilst being non-irritant to patient skin,
   wherein said at least one hypertonic composition consists of:
   dextrose provided in 50% (wt/wt);
   aqua as a moisturizer provided in 42.54% (wt/wt);
   glycerin as a humectant provided in 5% (wt/wt);
   xanthan gum as a thickener provided in 0.6% (wt/wt);
   hydroxyethylcellulose as a thickener provided in 0.6% (wt/wt);
   a mixture of phenoxyethanol, caprylyl glycol and chlorphenesin as a preservative provided in 0.6% (wt/wt); and
   sodium benzoate as a preservative provided in 0.1% (wt/wt);
   further wherein said hypertonic composition provides said TTO-based composition above 1700 mOsm/L.

2. A method of producing the non-irritating tea tree oil (TTO)-based topical therapeutic composition of claim 1, comprising at least one step of admixing components a, b, and c until a homogeneous composition is obtained.

3. A method of treating dermatology conditions in mammals comprising applying the non-irritating tea tree oil (TTO)-based topical therapeutic composition of claim 1 to mammals in need thereof.

* * * * *